United States Patent [19]

Renga et al.

[11] Patent Number: 4,554,372

[45] Date of Patent: Nov. 19, 1985

[54] PREPARATION OF CARBAMATES

[75] Inventors: James M. Renga, Walnut Creek; Roy A. Periana-Pillai, Berkeley, both of Calif.; Kevin A. Frazier, Midland, Mich.

[73] Assignee: The Dow Chemical Company, Midland, Mich.

[21] Appl. No.: 642,860

[22] Filed: Aug. 21, 1984

Related U.S. Application Data

[63] Continuation-in-part of Ser. No. 498,223, May 26, 1983, abandoned.

[51] Int. Cl.$^4$ ........................................... C07C 125/065
[52] U.S. Cl. .................................. 560/161; 260/465.4
[58] Field of Search ...................... 560/161; 260/465.4

[56] References Cited

U.S. PATENT DOCUMENTS 3,477,933  11/1969  Stamm ................................. 560/161

OTHER PUBLICATIONS

Mortimer, "Chemistry: A Conceptual Approach," pp. 74–78, (1967).
Driguiz, Can. J. Chem., 55, pp. 700–701, (1977).

Primary Examiner—Michael L. Shippen
Attorney, Agent, or Firm—Paul Bork; Douglas N. Deline

[57] ABSTRACT

2-Substituted alkyl (2-substituted alkyl)carbamates useful as intermediates in the preparation of epoxy derivatives of olefins are prepared by reacting 2-oxazolidones with an olefin and an electrophile such as halogen.

6 Claims, No Drawings

PREPARATION OF CARBAMATES

CROSS-REFERENCE TO RELATED APPLICATION

This is a continuation-in-part of application Ser. No. 498,223, filed May 26, 1983 and now abandoned.

BACKGROUND OF THE INVENTION

The present invention relates to a novel process. In particular, the present invention relates to a new process for forming 2-substituted alkyl (2-substituted alkyl)carbamates in high yield and selectivity.

The 2-haloalkyl (2-haloalkyl)carbamates have useful fungicidal and bactericidal properties. For example, it is known that treatment with 500 ppm of (2-chloroethyl)-methyl-2-chloroethyl ester completely inhibited growth of the following: *Lactobacillus casei, Erwinia amylovora, Fuso bact necrophorum* 10, *Piricularia oryzac, Aspergillus niger, Mucor miehei atcc* 16457, *Staphylococcus aureus atcc, Actinomyces viscosis, Clostridium perfringens, Clostridium septicum, Bacteroides fragilis, Bacteroides multiacidus, Streptococcus faecalis, Streptococcus bovis, Bacillus subtilis, Streptococcus mutans* and *Candida albicans nih*. Additionally, (2-chloroethyl)-(2-methoxylmethyl)-2-chloroethyl ester selectively completely inhibited symptoms of tobacco black shank when infected soil was planted after the soil was drenched in 25 ppm water solution of (2-chloroethyl)-(2-methoxymethyl)-2-chloroethyl ester.

It has been previously known to prepare 2-haloalkyl-N-(2-haloalkyl)carbamates by addition of 2-haloalkylamines to 2-haloalkyl haloformates. The following schematic representation illustrates this process.

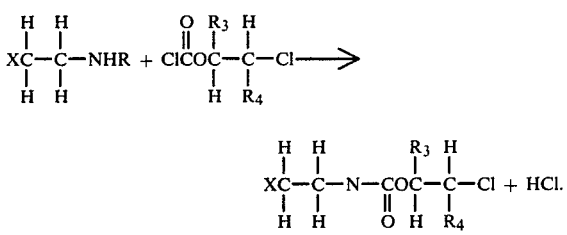

By substituting an alkyl trichloroacetate for the haloformate, the by-product is chloroform instead of hydrogen chloride, e.g.,

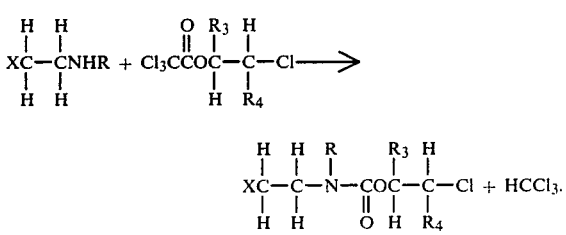

A second process disclosed by Dorschner et al., U.S. Pat. No. 3,885,954, employs the reaction of an isocyanate with an alcohol according to the following scheme:

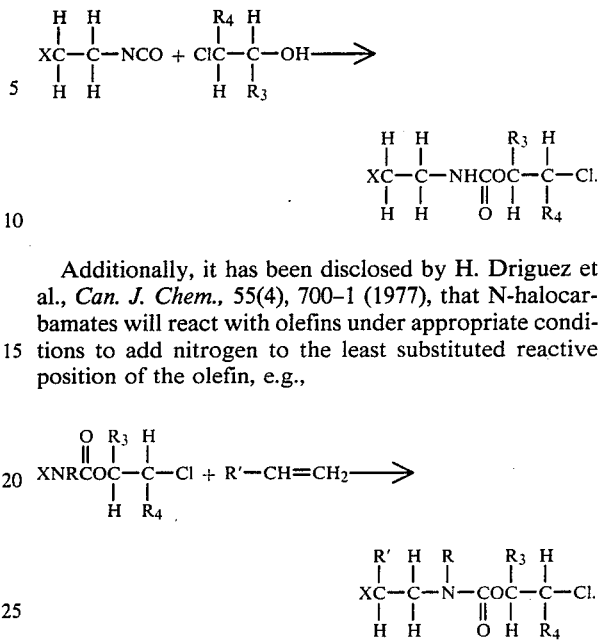

Additionally, it has been disclosed by H. Driguez et al., *Can. J. Chem.*, 55(4), 700–1 (1977), that N-halocarbamates will react with olefins under appropriate conditions to add nitrogen to the least substituted reactive position of the olefin, e.g.,

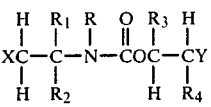

Previously known processes have employed starting materials that are expensive, unstable over long time periods or otherwise handled only with difficulty. In addition, the process of Dorschner et al. is limited to preparation of mono-N-substituted carbamates only.

It would be desirable to prepare 2-haloalkyl-N-(2-haloalkyl)carbamates in high yields and selectivity employing readily available and chemically stable oxazolidinones.

SUMMARY OF THE INVENTION

There is now provided a process for the preparation of 2-haloalkyl-N-(2-haloalkyl)carbamates corresponding to the formula:

$$\begin{array}{c} H\ R_1\ R\ O\ R_3\ H \\ |\ \ |\ \ |\ \ ||\ \ |\ \ | \\ XC-C-N-COC-CY \\ |\ \ |\ \ \ \ \ \ \ \ |\ \ | \\ H\ R_2\ \ \ \ \ \ \ \ H\ R_4 \end{array}$$

wherein
X is halo or cyano;
Y is halo or cyano, provided that when both X and Y are halo, then X is the more electronegative halo and when Y is halo, X must be halo;
R, $R_1$ and $R_2$ are independently hydrogen or $C_{1-10}$ alkyl or alkoxyalkyl; and
$R_3$ and $R_4$ are independently hydrogen or $C_{1-4}$ alkyl or haloalkyl, or $R_3$ and $R_4$ together constitute a $C_{3-4}$ alkylene group;
comprising contacting an oxazolidone corresponding to the formula:

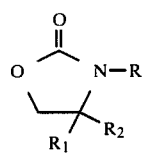

wherein R, $R_1$ and $R_2$ are as previously defined with an olefin corresponding to the formula:

$$R_3HC=CHR_4$$

wherein $R_3$ and $R_4$ are as previously defined and an electrophile XY wherein X and Y are as previously defined, at a temperature of from about 25° C. to about 100° C.

DETAILED DESCRIPTION OF THE INVENTION

The reactants employed in the process are an oxazolidone, an olefin and an electrophile. Any oxazolidone corresponding to formula I may suitably be employed. Preferred are compounds wherein $R_1$ and $R_2$ are hydrogen, e.g., 2-oxazolidone itself or an N-substituted oxazolidone such as N-methyl-, N-ethyl- or N-(2-methoxyethyl)-2-oxazolidone.

The olefin corresponding to formula II is preferably ethylene or a mono-substituted olefin, e.g., an olefin of formula II wherein $R_4$ is hydrogen. Examples include ethylene, propylene, allyl chloride, allyl bromide and cyclohexene.

The electrophile XY includes cyanogen, cyanogen halides, and halogens including mixed halogens such as iodochloride or bromine chloride. Preferred electrophiles are chlorine or bromine.

The reactants are combined in any order in a reaction vessel optionally in the presence of an inert solvent. Preferably the electrophile is added last in a controlled manner. Where the electrophile is gaseous, e.g., chlorine, it may be slowly bubbled through a mixture of the remaining reactants.

while any amount of reactants may be employed, suitably less than equal molar amounts of olefin and electrophile are reacted with the oxazolidone compound. In this manner the oxazolidone is employed as a solvent to retain the reactants and products in a workable condition. The product is easily removed from excess oxazolidone reactant after completion of the reaction. Preferred molar ratios of oxazolidone:olefin:electrophile are from about 1.0:0.1:0.1 to about 1.0:0.5:0.5.

Elevated pressures may be employed if desired, especially where gaseous reactants are employed. For example, a suitable pressurized reactor may be sealed and charged with chlorine gas along with the remaining reactants according to one embodiment hereof.

While temperatures from about 25° C. to about 100° C. may suitably be employed, optimum temperatures will depend on the reactants employed and are determined by lower working temperatures where the oxazolidone reactant is tractable and upper working temperatures selected to avoid dangerous conditions. Furthermore, by-products, such as those formed by direct electrophile addition to the olefin, are limited by use of reduced temperatures.

Complete reaction of the reactants is facilitated by slow addition of electrophilic reactant and vigorous agitation of the reaction mixture. No catalyst need be employed to initiate the reaction, however, use of a catalyst will not depart from the scope of the present invention.

It is furthermore possible to employ a solvent for the process if desired. However, increased amounts of olefin-electrophile addition products are observed where a solvent is employed. As suitable solvents, there may be enumerated methylene chloride, dimethyl formamide, N-methyl formamide, nitromethane, etc.

The reaction is continued until substantial amounts of the desired 2-haloalkyl-N-(2-haloalkyl)carbamate reaction product are formed. Generally, reaction times from about 1 hour to about 12 hours are suitably employed.

The product may be recovered by any suitable technique. Generally, the reaction mixture may be distilled directly or first washed with ethyl ether or other solvent and water and then distilled.

SPECIFIC EMBODIMENTS

Having described the invention, the following examples are provided as further illustrative and are not to be construed as limiting.

EXAMPLE 1

N-methyl-2-oxazolidone (200 g, 1.98 mole) is stirred magnetically at about 25° C. in a 500-ml 3-neck flask equipped with 2 sparger tubes and a vent to a gas bubbler. Ethylene and chlorine are introduced at equal rates (125 mmole/hour—determined by previously calibrated rotometers). With vigorous stirring, this rate allows for complete reaction of the gases in solution as evidenced by the lack of bubbling in the gas bubbler. The reaction is continued until 750 mmole of the respective gases have been added (about 6 hours). The solution is purged with $N_2$ to remove traces of HCl generated from any radical chlorination and diluted with ethyl ether and two washings with water to remove the excess starting material and ethylene dichloride by-product. Concentration and vacuum distillation then affords 115 g (575 mmole) of 2-chloroethyl (2-chloroethyl)methyl carbamate, b.p. 130° C.–131° C./8 mm.

EXAMPLES 2-9

The reaction conditions of Example 1 are substantially repeated employing oxazolidones and olefins having substituents as identified in the following Table I, and a halogen. Reaction temperatures slightly greater than the melting point of the oxazolidinone reactant are employed for ease of operation. Products, except where noted, are identified according to standard techniques of nuclear magnetic resonance spectroscopy and infrared absorption spectroscopy.

TABLE I

 $N-R + R_3HC=CHR_4 + X_2 \longrightarrow$ $$\begin{array}{c} H \;\; H \;\; R \;\;\;\;\;\;\; R_3 \;\; H \\ |\;\;\;|\;\;\;|\;\;\;\;\;\;\;\;\;\;|\;\;\;| \\ XC-C-N-COC-C-X \\ |\;\;\;|\;\;\;\;\;\;\;\;\;\;||\;\;\;|\;\;\;| \\ H \;\; H \;\;\;\;\;\;\;\; O \;\; H \;\; R_4 \end{array}$$

| Example | R | $R_3$ | $R_4$ | X | b.p. (°C./mm Hg) |
|---|---|---|---|---|---|
| 2 | H | H | H | Cl | 87–96/0.2 |
| 3 | H | $CH_3$ | H | Cl | 134–8/5.3 |
| 4 | $CH_3$ | H | H | Cl | 130.5/8.0 |
| 5 | $CH_3$ | $CH_3$ | H | Cl | 110/3.5 |
| 6 | $C_2H_5$ | H | H | Cl | 127–8/6.0 |
| 7 | $CH_2CH_2OCH_3$ | H | H | Cl | 151–3/5.5 |
| 8 | $CH_3$ | $-(CH_2)_4-$ | — | Cl | 132–4/0.4 |
| 9 | $CH_3$ | $CH_2Br$ | H | Br | — |

EXAMPLES 10-15

The reaction conditions of Example 1 are again substantially repeated employing various olefins, chlorine and the 2-oxazolidone reactants further identified by means of the substituents as provided in Table II. Isolated products are identified by standard techniques of nuclear magnetic resonance spectroscopy and infrared absorption spectroscopy. Conversions are based on moles of oxazolidone reactant and determined from gas-liquid chromatographic data. Isolated yields are based on amounts of product formed. The method of isolation is by direct distillation of the product mixture. Results are contained in Table II.

TABLE II $$\underset{A}{\overset{O}{\underset{\diagdown\diagup}{O\overset{\parallel}{\diagup\diagdown}N-R}}} + \underset{B}{R_3HC=CH_2} + \underset{C}{Cl_2} \longrightarrow ClC\underset{H}{\overset{H}{\underset{|}{-}}}\overset{H}{\underset{H}{\underset{|}{-}}}C-N-\overset{O}{\underset{\parallel}{C}}O\overset{R_3}{\underset{H}{\underset{|}{-}}}\overset{H}{\underset{H}{\underset{|}{-}}}C-Cl + R_3XCHCH_2X$$

| | A | B | C | | D | E | |
|---|---|---|---|---|---|---|---|
| | | | moles | | | | % Isolated |
| Example | R | $R_3$ | A | B* | C* | Time (hr) | % Conv. | % Sel.** | Yield |
| 10 | $CH_3$ | H | 0.25 | 0.16 | .016 | 6.5 | 59.7 | 84.1 | 95.1 |
| 11 | $CH_3$ | H | 2.0 | 0.33 | 0.33 | 5.0 | 15.1 | 92.2 | — |
| 12 | $CH_3$ | $CH_3$ | 2.0 | 1.6 | 1.6 | 10.0 | 65.1 | 81.8 | 89.4 |
| 13 | $CH_3$ | $CH_3$ | 2.0 | 0.5 | 0.5 | 6.0 | 21.4 | 84.4 | 96.7 |
| 14 | $C_2H_5$ | H | 0.22 | 0.08 | 0.08 | 3.0 | 29.4 | 89.9 | 83.1 |
| 15 | $CH_2CH_2OCH_3$ | H | 0.17 | 0.10 | 0.10 | 7.0 | 27.1 | 53.7 | 98.3 |

*Estimated from flow rate.
**Selectivity to desired carbamate.

What is claimed is:

1. A process for the preparation of 2-substituted alkyl (2-substituted alkyl)-carbamates corresponding to the formula:

$$XC\overset{H}{\underset{H}{\underset{|}{-}}}\overset{R_1}{\underset{R_2}{\underset{|}{-}}}C\overset{R}{\underset{|}{-}}N\overset{O}{\underset{\parallel}{-}}CO\overset{R_3}{\underset{H}{\underset{|}{-}}}\overset{H}{\underset{R_4}{\underset{|}{-}}}CY$$

wherein
X and Y are halo, providing that if X and Y are not the same halo the V is the more electronegative halo,
R, $R_1$ and $R_2$ are independently hydrogen or $C_{1-10}$ alkyl or alkoxyalkyl; and
$R_3$ and $R_4$ are independently hydrogen or $C_{1-4}$ alkyl or haloalkyl and together may form a $C_{3-4}$ alkylene group, comprising contacting an oxazolidone corresponding to the formula:

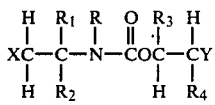

wherein R, $R_1$ and $R_2$ are as previously defined, with an olefin corresponding to the formula:

$$R_3HC=CHR_4$$

where $R_3$ and $R_4$ are as previously defined and an electrophile XY where X and Y are as previously defined at a temperature from about 25° C. to about 100° C.

2. A process according to claim 1 wherein $R_1$ and $R_2$ are hydrogen.

3. A process according to claim 2 wherein the oxazolidone is 2-oxazolidone, N-methyl-2-oxazolidone, N-ethyl-2-oxazolidone or N-methoxyethyl-2-oxazolidone.

4. A process according to claim 1 wherein the olefin is ethylene, propylene, allyl chloride, allyl bromide or cyclohexene.

5. A process according to claim 1 wherein the electrophile is chlorine or bromine.

6. A process according to claim 1 wherein less than equal molar amounts of olefin and electrophile based on the amount of oxazolidone reactant are contacted with the oxazolidone reactant.

* * * * *

UNITED STATES PATENT AND TRADEMARK OFFICE
CERTIFICATE OF CORRECTION

PATENT NO. : 4,554,372

DATED : November 19, 1985

INVENTOR(S) : James M. Renga; Ray A. Periana-Pillai; Kevin A. Frazier

It is certified that error appears in the above-identified patent and that said Letters Patent is hereby corrected as shown below:

In column 1, lines 28-29, please delete "(2-chloroethyl)-(2-methoxylmethyl)-2-chloroethyl" and insert therefor -- (2-chloroethyl)-(2-methoxymethyl)-2-chloroethyl --.

At column 3, line 3, it should look like the following: -- $R_3HC=CHR_4$    II --.

At column 3, line 35, please delete "while" and insert therefor -- While --.

In column 5, Claim 1, line 47, please delete "the V" and insert therefor -- then X --.

Signed and Sealed this

Twenty-fourth Day of June 1986

[SEAL]

Attest:

DONALD J. QUIGG

Attesting Officer       Commissioner of Patents and Trademarks